US012740703B2

(12) United States Patent
Lee et al.

(10) Patent No.: US 12,740,703 B2
(45) Date of Patent: Sep. 22, 2026

(54) OPTICAL MICROSCOPE FOR RETINAL IMAGING

(71) Applicant: ELECTRONICS AND TELECOMMUNICATIONS RESEARCH INSTITUTE, Daejeon (KR)

(72) Inventors: Sang Kyun Lee, Daejeon (KR); Dong Hoon Song, Daejeon (KR); Chul Huh, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 304 days.

(21) Appl. No.: 18/589,113

(22) Filed: Feb. 27, 2024

(65) Prior Publication Data

US 2024/0285164 A1 Aug. 29, 2024

(30) Foreign Application Priority Data

Feb. 28, 2023 (KR) ........................ 10-2023-0026688

(51) Int. Cl.
*A61B 3/13* (2006.01)
*A61B 3/12* (2006.01)
(Continued)

(52) U.S. Cl.
CPC .............. *A61B 3/13* (2013.01); *A61B 3/1225* (2013.01); *B06B 1/067* (2013.01); *G02B 21/0012* (2013.01); *B06B 2201/76* (2013.01)

(58) Field of Classification Search
CPC ........... A61B 3/13; A61B 3/1225; A61B 8/10; A61B 8/4494; B06B 1/067; B06B 2201/76; B06B 1/0677; G02B 21/0012
(Continued)

(56) References Cited

U.S. PATENT DOCUMENTS 5,880,012 A 3/1999 Ha et al.
7,719,760 B2 5/2010 Kim et al.
(Continued)

FOREIGN PATENT DOCUMENTS

CN 116237224 A * 6/2023 ........... B06B 1/0662
KR 10-2021-0034466 A 3/2021
KR 10-2316306 B1 10/2021

OTHER PUBLICATIONS

Haemin Kim et al., “Deep laser microscopy using optical clearing by ultrasound-induced gas bubbles,” Photonics, Sep. 5, 2022, pp. 762-768, vol. 16.

*Primary Examiner* — Tuyen Tra

(57) ABSTRACT

The present invention proposes a technology that enables in vivo imaging while expanding the penetration depth of light into the tissue in an ultrasound-induced optical clearing microscopy (USOCM) system using an optical microscope, in particular, a non-linear optical microscope such as a two-photon microscope, and an ultrasonic transducer. For maximum efficiency, the ultrasonic transducer should be positioned between an optical microscope (objective lens) and the sample. In this case, since an existing ultrasonic transducer is opaque, a laser beam of an optical microscope using an ultrashort laser system cannot pass through the existing ultrasonic transducer. In order to solve such a problem, a transparent ultrasonic transducer is applied such that there is no problem in a laser beam passing therethrough and reaching a sample.

17 Claims, 5 Drawing Sheets

(51) Int. Cl.
*B06B 1/06* (2006.01)
*G02B 21/00* (2006.01)

(58) Field of Classification Search
USPC .................................................. 351/200, 205
See application file for complete search history.

(56) References Cited

U.S. PATENT DOCUMENTS

| | | | | |
|---|---|---|---|---|
| 8,016,419 | B2 | 9/2011 | Zhang et al. | |
| 2013/0245406 | A1* | 9/2013 | Wang | A61B 5/0068 600/317 |
| 2013/0338478 | A1* | 12/2013 | Hirota | A61B 5/0095 600/407 |
| 2024/0016389 | A1* | 1/2024 | Jiang | A61B 8/4477 |

* cited by examiner

OPTICAL MICROSCOPE FOR RETINAL IMAGING

CROSS-REFERENCE TO RELATED APPLICATION

This application claims priority to and the benefit of Korean Patent Application No. 10-2023-0026688, filed on Feb. 28, 2023, the disclosure of which is incorporated herein by reference in its entirety.

BACKGROUND

1. Field of the Invention

The present invention provides an optical microscope such as a non-linear multi-photon microscope that is usable for retinal imaging for diagnosing ocular disease, Alzheimer's disease, pre-senile dementia (mild cognitive impairment), or the prognosis of preclinical Alzheimer's disease.

2. Discussion of Related Art

Retinal imaging or image acquisition may be used for diagnosing ocular disease, Alzheimer's disease (AD), pre-senile dementia (mild cognitive impairment (MCI), or the prognosis of preclinical AD. The early stage of AD may be detected by scanning the retina to detect amyloid plaques and tau tangles accumulated in the ocular fundus.

Many optical apparatuses for such retinal imaging have been developed and are being applied in actual clinical fields. Among the optical apparatuses, an optical coherence tomography (OCT) apparatus is one of the representative apparatuses. OCT apparatuses may image each layer of the retina using back-scattering of light according to a difference in refractive index. OCT apparatuses are less affected by eye movement due to a fast scanning speed and thus are widely used as in vivo imaging apparatuses in the ophthalmology fields. However, since AD diagnosis using OCT apparatuses is made through a change in thickness of each layer of OCT, the particularity of AD diagnosis has not yet been secured.

A scanning laser ophthalmoscope (SLO) apparatus attempts to diagnose AD from the retina using spontaneous fluorescence or an exogenous fluorescent body (curcumin or the like), but a light source in a visible light range should be used, the SLO apparatus has the disadvantage of being vulnerable to photobleaching or photo-damage.

Similar to SLO apparatuses, much research is being conducted using an optical microscope, in particular, a non-linear optical microscope as an apparatus that attempts to diagnose AD in the retina using spontaneous fluorescence or an exogenous fluorescent body. This is because non-linear optical microscopes such as multi-photon microscopes, for example, two-photon microscopes (TPMs), can overcome the limitations of the above-described SLO apparatuses.

Meanwhile, by using a technology capable of generating an air bubble layer in a desired area within biological tissue using ultrasonic waves and a technology capable of maintaining the generated air bubbles while obtaining an image, ultrasound-induced optical clearing microscopy (USOCM), which is capable of securing an imaging depth 6 times or more than that of the existing technology) was developed.

Referring to FIG. 1, in USOCM, ultrasonic waves 30 are radiated onto a biological tissue sample 10 using an ultrasonic transducer 20 to generate micrometer-sized air bubbles 40 in the biological tissue, and the penetration depth of light into the tissue is increased using a phenomenon in which the generated air bubbles 40 scatter light in a traveling direction of light (Source: "DGIST, Development Of Ultrasound Tissue Transparency Technology . . . " https://mdtoday-.co.kr/news/view/1065597043300582).

An image is acquired by focusing a laser beam 60 on a target portion 15 of the sample 10 through an objective lens 50 of an optical microscope. However, the USOCM has the disadvantage that in vivo measurement is difficult because the ultrasonic transducer 20 is positioned in a direction opposite to the objective lens 50 of the optical microscope with the sample 10 interposed therebetween.

SUMMARY OF THE INVENTION

When a sample is observed using ultrasound-induced optical clearing microscopy (USOCM), in vivo imaging is difficult when an ultrasonic transducer is positioned behind or next to the sample as shown in FIG. 1, and in vivo imaging is possible when the ultrasonic transducer is positioned at the same position as the sample. For example, when a human eyeball is observed, an objective lens of an optical microscope is positioned in front of the eyeball (front of the face) and an ultrasonic transducer is positioned next to the eyeball (the face) or behind the cerebrum (the head), resulting in a decrease in effectiveness of an ultrasonic sensor.

To solve the problems, the present invention is directed to providing a technology that enables in vivo imaging while expanding the penetration depth of light into the tissue in a USOCM system using an optical microscope, in particular, a non-linear optical microscope such as a two-photon microscope and an ultrasonic transducer.

To solve the object, it is most preferable that an ultrasonic transducer be positioned in front of a sample to be observed. However, when the ultrasonic transducer is positioned in front of the sample to be observed so as to exhibit maximum efficiency, the ultrasonic transducer should be positioned between an optical microscope (objective lens) and the sample. In this case, since an existing ultrasonic transducer is opaque, a laser beam of an optical microscope using an ultrashort laser system cannot pass through the existing ultrasonic transducer. In order to solve such a problem, a transparent ultrasonic transducer is applied such that there is no problem in a laser beam passing therethrough and reaching a sample.

An optical microscope of the present invention may be preferably a multi-photon microscope, for example, a non-linear optical microscope such as a two-photon microscope (TPM). In addition, the optical microscope of the present invention may use an ultrashort laser system.

Specifically, according to an aspect of the present invention, there is provided an optical microscope for radiating a laser beam onto a sample and radiating ultrasonic waves onto the sample to observe the sample through an objective lens, the optical microscope including a transparent ultrasonic transducer through which the laser beam passes.

According to another aspect of the present invention, there is provided a transparent ultrasonic transducer which is used in an optical microscope for radiating a laser beam onto a sample and observing the sample through an objective lens, generates ultrasonic waves to radiate the generated ultrasonic waves onto the sample, and allows the laser beam to be transmitted.

The optical microscope of the present invention may be a non-linear optical microscope including a multi-photon microscope, but is not limited thereto.

In addition, the transparent ultrasonic transducer may be positioned between the sample and the objective lens, but the present invention is not limited thereto.

The transparent ultrasonic transducer may include a transparent piezoelectric material, a matching layer positioned outside the transparent piezoelectric material to face the sample, and a glass slide positioned outside the transparent piezoelectric material to face the objective lens. Here, the glass slide may include a curved surface that allows focusing of the laser beam to be adjusted with respect to the sample.

In addition, the transparent ultrasonic transducer may include a glass slide having a curved surface that allows focusing of the laser beam to be adjusted with respect to the sample.

The transparent ultrasonic transducer may further include an acoustic lens that allows acoustic focusing of the ultrasonic waves to be performed with respect to the sample. In this case, the acoustic lens may include an acoustic hole through which the laser beam passes.

In addition, the transparent ultrasonic transducer itself may be manufactured in a curved shape.

The above-described configurations and operations of the present invention will become more apparent from embodiments described in detail below with reference to the accompanying drawings.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Advantages and features of the present invention and methods for achieving them will be made clear from embodiments described in detail below with reference to the accompanying drawings. However, the present invention may be embodied in many different forms and should not be construed as being limited to the embodiments set forth herein. Rather, these embodiments are provided so that this disclosure will be thorough and complete and will fully convey the scope of the present invention to those of ordinary skill in the technical field to which the present invention pertains. The present invention is defined by the claims. Meanwhile, terms used herein are for the purpose of describing the embodiments and are not intended to limit the present invention. As used herein, the singular forms include the plural forms as well unless the context clearly indicates otherwise. The term “comprise” or “comprising” used herein does not preclude the presence or addition of one or more other elements, steps, operations, and/or devices other than stated elements, steps, operations, and/or devices.

Figure 1:
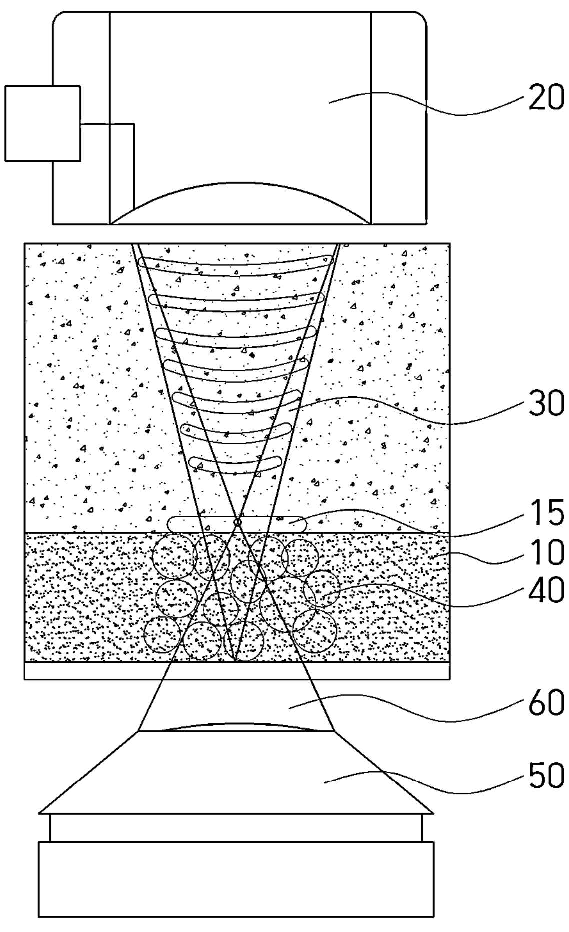
FIG. 1 is a conceptual view for describing ultrasound-induced optical clearing microscopy (USOCM)
Figure 2:
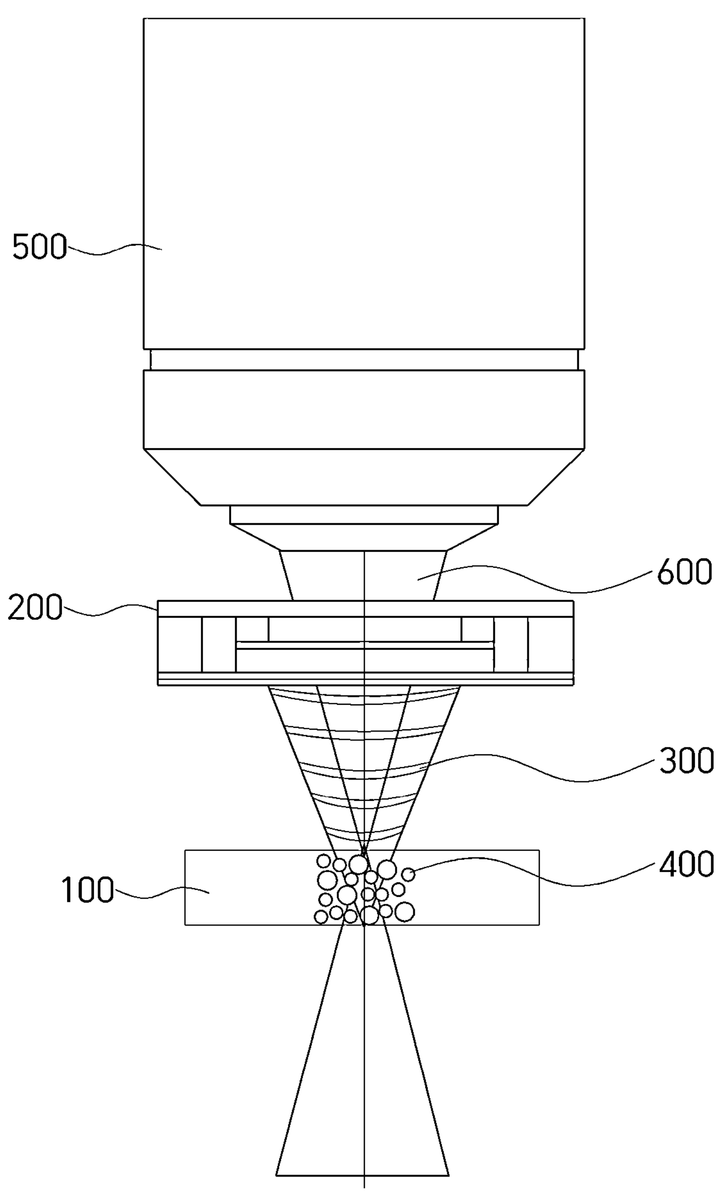
FIG. 2 is a conceptual view for describing an optical microscope according to an embodiment of the present invention.

FIG. 2 is a conceptual view for describing an optical microscope according to an embodiment of the present invention. FIG. 2 is a schematic view of a structure in which a transparent ultrasonic transducer that generates air bubbles of ultrasound-induced optical clearing microscopy (USOCM) and a non-linear optical microscope such as a two-photon microscope are coupled to achieve in vivo imaging which is the purpose of the present invention.

Referring to FIG. 2, it can be seen that an ultrasonic transducer 200 is positioned between a bio sample 100 and an objective lens 500 to radiate ultrasonic waves 300 onto the bio sample 100 and generate air bubbles 400. In this case, since the laser beam 600 should be radiated onto the bio sample 100 through the objective lens 500, the ultrasonic transducer 200 should be transparent.

Figure 3:
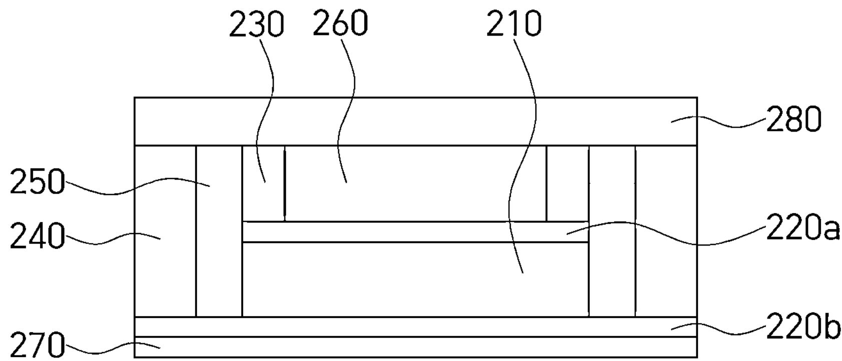
FIG. 3 is a structural view of a transparent ultrasonic transducer according to an embodiment of the present invention.

FIG. 3 illustrates a detailed structure of a transparent ultrasonic transducer 200 according to an embodiment of the present invention.

Basically, the transparent ultrasonic transducer 200 is formed in a layered form including a transparent piezoelectric material 210, a transparent upper electrode **220*a*, and a transparent lower electrode 220*b* and thus is configured to allow a laser beam 600 to be transmitted (see FIG. 2**).

Lead magnesium niobate-lead titanate (PMN-PT) may be used as the transparent piezoelectric material 210.

Regarding an internal structure, an internal electrode 230 is perpendicularly connected to the transparent upper electrode **220*a*, and an external electrode 240 is perpendicularly connected to the transparent lower electrode 220*b*. The internal electrode 230 and the external electrode 240 are insulated from each other by a vertical insulator 250. The internal electrode 230 is supported by a backing layer 260**.

As an ultimately exposed structure, a transparent matching layer 270, which is an ultimately exposed surface facing a bio sample 100, is positioned on an outer surface of the lower electrode **220*b*, and a transparent glass slide 280, which is an ultimately exposed surface facing an objective lens 500, is positioned on outer surfaces of the internal electrode 230, the external electrode 240, and the backing layer 260**.

Figure 4:
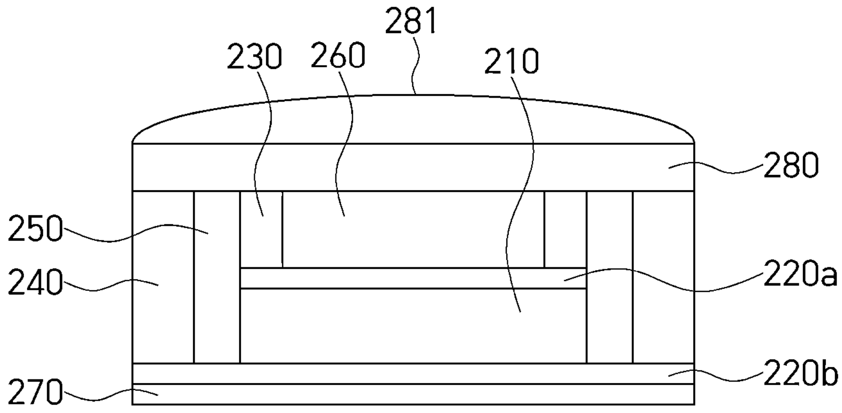
FIG. 4 is a structural view of a transparent ultrasonic transducer according to another embodiment of the present invention.

FIG. 4 is a configuration view of a transparent ultrasonic transducer 200 according to another embodiment.

The transparent ultrasonic transducer 200 has a structure in which an outer surface of a glass slide 280 is formed as a curved surface 281 to adjust the focusing of a laser beam 600 in a bio sample 100. Although the curved surface 281 is shown as a convex surface in FIG. 4, the present invention is not limited thereto. According to an optical design, the curved surface 281 may be a concave surface or an irregular surface.

Figure 5:
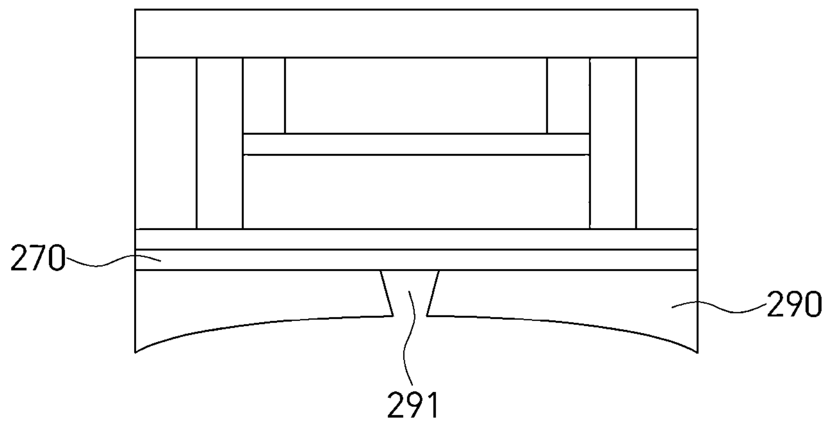
FIG. 5 is a structural view of a transparent ultrasonic transducer according to still another embodiment of the present invention.

FIG. 5 is a configuration view of a transparent ultrasonic transducer 200 according to still another embodiment.

An acoustic lens 290 was additionally installed on an outer surface of a matching layer 270 to enable the ultrasonic transducer 200 to perform additional acoustic focusing. An acoustic hole 291 is formed in the acoustic lens 290 to allow a laser beam 600 to pass therethrough. By providing the acoustic lens 290, the formation of air bubbles 400 (see FIG. 2) of the ultrasonic transducer 200 in a bio sample 100 is promoted.

Figure 6:
FIG. 6 is a structural view of a transparent ultrasonic transducer according to yet another embodiment of the present invention.

FIG. 6 is a configuration view of a transparent ultrasonic transducer 200 according to yet another embodiment.

Instead of using an acoustic lens 290 that performs acoustic focusing of an ultrasonic transducer 200 as shown in FIG. 5, the ultrasonic transducer 200 itself was manufactured to have a shape with a curvature, and thus a separate acoustic lens 290 and acoustic hole 291 were not required. In FIG. 6, an internal electrode 230, an external electrode 240, and an insulator 250 were omitted.

The embodiment of the optical microscope of FIG. 2 may be modified by arraying a plurality of transparent ultrasonic transducers 200 of various types described above.

The array of the transducers 200 may be implemented in a phased array method which is applied to a phased array antenna or radar. For example, a phase adjuster (not shown) may be assigned to each of the arrayed transducers 200 and the phase adjusters may be controlled so that each transducer 200 simultaneously generates laser beams with different phase differences. By adjusting the phase differences, the irradiation direction of the laser beam (600 in FIG. 2) can be changed as desired. As a result, the focusing position of the laser beam 600 irradiated to the sample 100 may be changed along the thickness of the sample 100 (i.e., the vertical direction in FIG. 2), so that image scanning in the thickness direction of the sample 100 becomes possible, without physically modifying the transducer 200, allowing more precise retinal images to be obtained.

Figure 7:
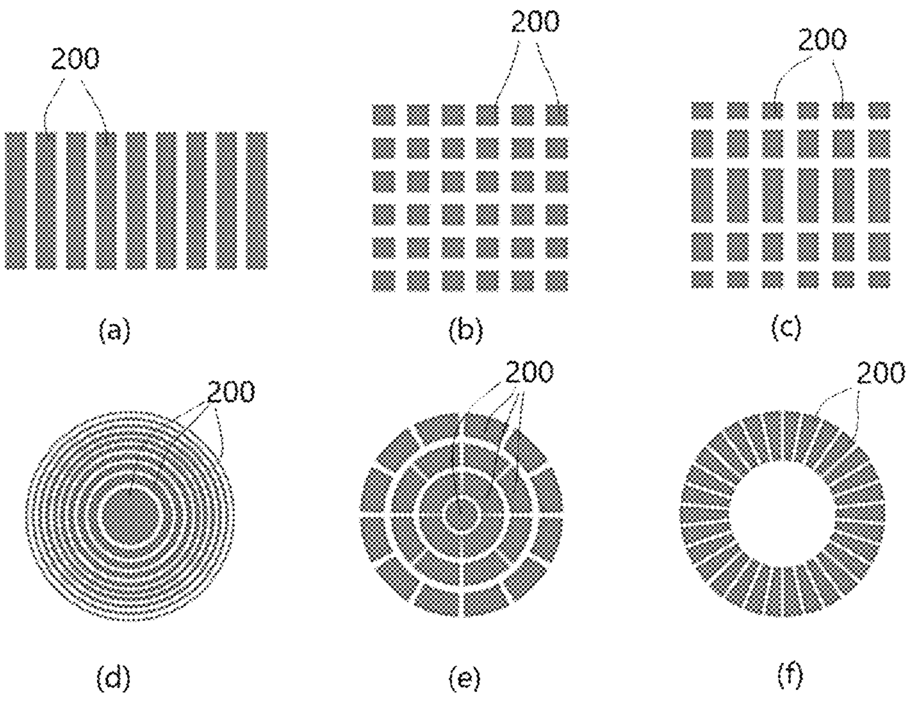
FIG. 7 shows examples of an arrangement of multiple transparent ultrasonic transducers for controlling the laser beam focusing positions.

FIG. 7 shows examples of an arrangement of multiple transparent ultrasonic transducers for controlling the laser beam focusing positions, in which (a), (b), and (c) illustrate that the transparent ultrasonic transducers 200 are arrayed in an approximately square shape, and (d), (e), and (f) illustrate the transducers 200 are arrayed in an approximately circular shape. The sizes or shapes of the arrayed transparent ultrasonic transducers 200 may either be the same (a, b, f) or be different (c, d, e). In the latter case, the different sizes or shapes may depend on the design of the beam focusing position, intensity, pattern, etc. of each transparent ultrasonic transducer 200.

According to the present invention, air bubbles can be formed in a bio sample, and by using the air bubbles, the penetration depth to which imaging can be performed by an existing non-linear optical microscope can be increased as compared with the related art. Also, by using a transparent ultrasonic transducer, in vivo imaging is enabled for a bio sample.

In addition, a structure of a transparent ultrasonic transducer is variously changed into various structures capable of performing laser beam focusing, ultrasonic focusing, or the like, thereby further improving the performance of an optical microscope system, in particular, a nonlinear optical microscope.

Embodiments in which the spirit of the present invention is specifically implemented have been described above. However, the technical scope of the present invention is not limited to the embodiments and accompanying drawings described above. The technical scope is to be determined by reasonable interpretation of the claims.

What is claimed is:

1. An optical microscope for radiating a laser beam onto a sample and observing the sample through an objective lens, the optical microscope comprising a transparent ultrasonic transducer which radiates ultrasonic waves onto the sample and through which the laser beam passes, wherein the transparent ultrasonic transducer comprises a plurality of transparent ultrasonic transducers, and wherein the plurality of transparent ultrasonic transducers are arrayed in a phased array method to change the focusing position of the laser beam along a thickness of the sample.

2. The optical microscope of claim 1, wherein the optical microscope is a non-linear optical microscope including a multi-photon microscope.

3. The optical microscope of claim 1, wherein the transparent ultrasonic transducer is positioned between the sample and the objective lens.

4. The optical microscope of claim 1, wherein the transparent ultrasonic transducer includes:

a transparent piezoelectric material;

a matching layer positioned outside the transparent piezoelectric material to face the sample; and a glass slide positioned outside the transparent piezoelectric material to face the objective lens.

5. The optical microscope of claim 4, wherein the glass slide includes a curved surface that allows focusing of the laser beam to be adjusted with respect to the sample.

6. The optical microscope of claim 4, wherein the transparent ultrasonic transducer further includes an acoustic lens that allows acoustic focusing of the ultrasonic waves to be performed with respect to the sample.

7. The optical microscope of claim 6, wherein the acoustic lens includes an acoustic hole through which the laser beam passes.

8. The optical microscope of claim 1, wherein the transparent ultrasonic transducer includes a glass slide having a curved surface that allows focusing of the laser beam to be adjusted with respect to the sample.

9. The optical microscope of claim 1, wherein the transparent ultrasonic transducer includes an acoustic lens that allows acoustic focusing of the ultrasonic waves to be performed with respect to the sample.

10. The optical microscope of claim 9, wherein the acoustic lens includes an acoustic hole through which the laser beam passes.

11. The optical microscope of claim 1, wherein the transparent ultrasonic transducer has a curvature shape.

12. A transparent ultrasonic transducer which is used in an optical microscope for radiating a laser beam onto a sample and observing the sample through an objective lens, generates ultrasonic waves to radiate the generated ultrasonic waves onto the sample, and allows the laser beam to be transmitted, the transparent ultrasonic transducer comprising an acoustic lens that allows acoustic focusing of the ultrasonic waves to be performed with respect to the sample, wherein the acoustic lens includes an acoustic hole through which the laser beam passes.

13. The transparent ultrasonic transducer of claim 12, wherein the transparent ultrasonic transducer is positioned between the sample and the objective lens.

14. The transparent ultrasonic transducer of claim 12, comprising:

a transparent piezoelectric material configured to generate the ultrasonic waves;

a matching layer positioned outside the transparent piezoelectric material to face the sample; and a glass slide positioned outside the transparent piezoelectric material to face the objective lens.

15. The transparent ultrasonic transducer of claim 14, wherein the glass slide includes a curved surface that allows focusing of the laser beam to be adjusted with respect to the sample.

16. The transparent ultrasonic transducer of claim 12, comprising a glass slide having a curved surface that allows focusing of the laser beam to be adjusted with respect to the sample.

17. The transparent ultrasonic transducer of claim 12, wherein the transparent ultrasonic transducer has a curvature shape.

* * * * *